(12) United States Patent
Glacer et al.

(10) Patent No.: US 12,241,880 B2
(45) Date of Patent: Mar. 4, 2025

(54) METHOD OF CONTROLLING HEATER SYSTEMS

(71) Applicant: Infineon Technologies AG, Neubiberg (DE)

(72) Inventors: Christoph Glacer, Munich (DE); Guillaume Dumas, Munich (DE); Johannes Manz, Munich (DE)

(73) Assignee: Infineon Technologies AG, Neubiberg (DE)

( * ) Notice: Subject to any disclaimer, the term of this patent is extended or adjusted under 35 U.S.C. 154(b) by 407 days.

(21) Appl. No.: 17/499,285

(22) Filed: Oct. 12, 2021

(65) Prior Publication Data

US 2022/0137016 A1 May 5, 2022

(30) Foreign Application Priority Data

Oct. 29, 2020 (EP) .................................... 20204685

(51) Int. Cl.
*G01N 33/00* (2006.01)
*G01N 21/17* (2006.01)
(Continued)

(52) U.S. Cl.
CPC ..... *G01N 33/0016* (2013.01); *G01N 21/3504* (2013.01); *G01N 21/3577* (2013.01);
(Continued)

(58) Field of Classification Search
CPC ........... G01N 33/0016; G01N 21/3504; G01N 21/3577; G01N 29/02; G01N 29/2418; G01N 33/0062; G01N 33/0073; G01N 2021/1704; G01N 2291/02809; G01N 2201/06186; G01N 29/326; G01N 21/1702; G01N 21/255; G01N 21/27; G01N 21/314; G01N 21/61
See application file for complete search history.

(56) References Cited

U.S. PATENT DOCUMENTS 8,061,149 B1 * 11/2011 Gowans ................. A61J 1/165
62/3.62
2009/0009769 A1 1/2009 Uber et al.
(Continued)

*Primary Examiner* — David E Smith
*Assistant Examiner* — Christopher J Gassen
(74) *Attorney, Agent, or Firm* — Slater Matsil, LLP

(57) ABSTRACT

An emitter for emitting radiations at a specific wavelength includes a Joule-heated emitting electrical conductor to emit radiations at an emission temperature, a controller to control a variable voltage subjected to the Joule-heated emitting electrical conductor and modulated according to a duty cycle, the duty cycle being variable between a high-average power duty cycle during hot periods, so that the Joule-heated emitting electrical conductor is subjected to a high-average power to reach and maintain the emission temperature; and a low-average power duty cycle during cold periods alternated to the hot periods, so that the Joule-heated emitting electrical conductor is subjected to a low-average power to reach a temperature smaller than the emission temperature, wherein the high-average power duty cycle and the low-average power duty cycle is defined based on a temperature-indicative measured value indicative of the ambient temperature as measured.

15 Claims, 8 Drawing Sheets

(51) Int. Cl.
*G01N 21/3504* (2014.01)
*G01N 21/3577* (2014.01)
*G01N 29/02* (2006.01)
*G01N 29/24* (2006.01)

(52) U.S. Cl.
CPC ......... *G01N 29/02* (2013.01); *G01N 29/2418* (2013.01); *G01N 33/0062* (2013.01); *G01N 33/0073* (2013.01); *G01N 2021/1704* (2013.01); *G01N 2291/02809* (2013.01)

(56) References Cited

U.S. PATENT DOCUMENTS

2015/0300944 A1 10/2015 Pelletier et al.
2020/0300698 A1 9/2020 Wakuda

* cited by examiner

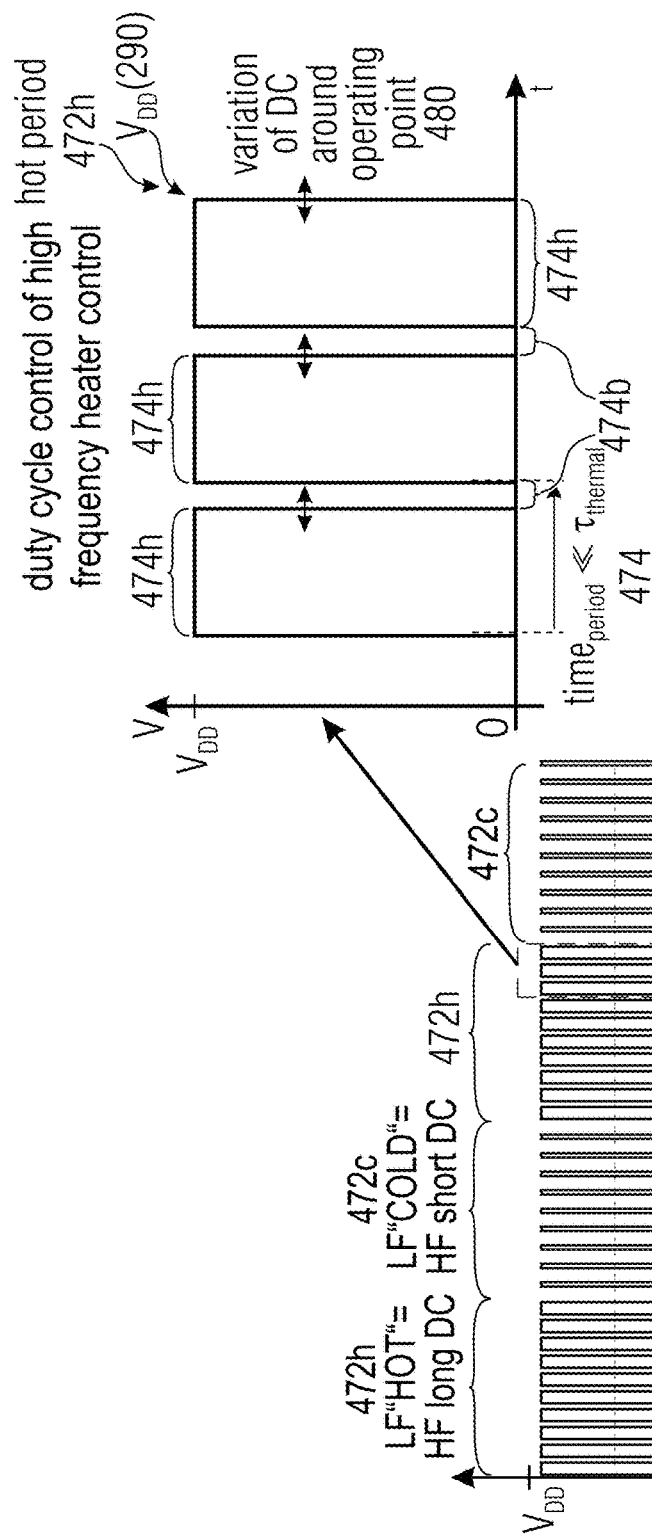
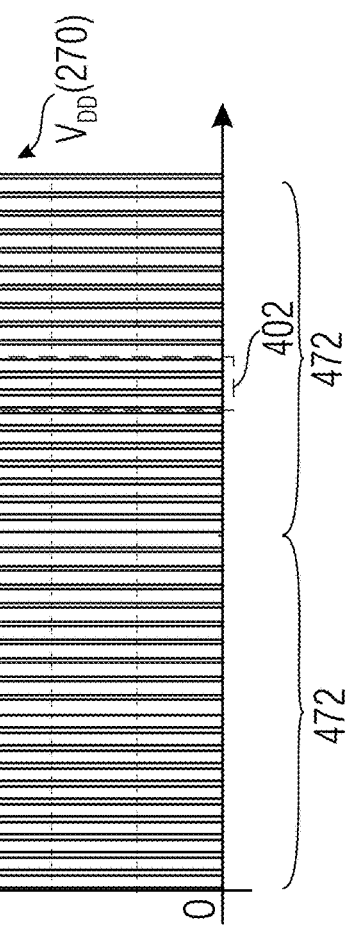
Fig. 4b
Fig. 4a

METHOD OF CONTROLLING HEATER SYSTEMS

This application claims the benefit of European Patent Application No. 20204685.0, filed on Oct. 29, 2020, which application is hereby incorporated herein by reference.

TECHNICAL FIELD

Examples hereinbelow refer to emitters, sensors and detectors, e.g. for fluid sensing. Examples also relate to emitting methods, and/or sensing methods which perform emitting methods or sensing methods, and non-transitory storage units storing instructions which, when running on a computer, perform emitting methods or sensing methods.

An example refers to an emitter for emitting radiations, e.g. a visible light emitter or infrared (IR) emitter or mid IR (MIR) emitter.

An example refers to a fluid sensor, such as gas sensor. The fluid sensor may include an emitter and a detector. The detector may be a photoacoustic sensor (PAS), a light sensor, an infrared (IR), and more in particular a MIR sensor.

Examples refer to an emitting method and a sensing method, e.g. for measuring the concentration of a fluid (e.g., a gas).

BACKGROUND

A fluid sensor (e.g., a gas sensor) may be used for detecting the quantity of a target fluid in a target environment. The fluid sensor may be, for example, a micro mechanical electric system (MEMS) device, and may imply the use of a microcontroller.

A fluid sensor may comprise an emitter for emitting radiations at a particular wavelength onto a target environment. The target environment is in general replenished with a target fluid, whose amount (or concentration) is to be measured. The radiations shall have a specific wavelength associated to the target fluid, to excite the molecules or atoms at their characteristic wavelength (e.g., wavelength of maximum absorption typical of a target gas). A detector, downstream to the target environment, is illightened by the radiations propagated through the target environment. At the detector, an electric signal indicative of the propagated radiations is measured. From the electric signal, the amount or concentration of the target fluid in the target environment is obtained.

In some cases, the detector is a photoacoustic detector including a microphone. The microphone includes a microphone membrane which is either inside the target environment or is inside a sealed environment replenished with a reference fluid. In any case, pressure of the target fluid and/or reference fluid changes by virtue of the photoacoustic effect, i.e. by virtue of a change in pressure (inside the target environment or is inside the sealed environment), caused by the interaction of the radiation (at the specific wavelength) with the molecules of the target fluid and/or reference fluid. The change in pressure is an acoustic wave, which deforms the microphone membrane, causing the generation of an electric signal indicative of the acoustic wave. The acoustic wave is associated to the impinging radiation, which is in turn associated to the amount or concentration of the target fluid. Hence, by analyzing the electric signal generated by the microphone, it is possible to arrive at having information on the amount or concentration of the target fluid.

In other cases (e.g., for non-dispersive infrared, NDIR, sensors), the detector may be a thermal detector, and perform thermal measurements associated to the impinging radiation at the specific wavelength, also arriving at a measurement of the amount or concentration of the target fluid.

The emitter may include an electrical conductor, which dissipates electric power by Joule effect, irradiating the target environment with radiation at different wavelengths in accordance to the temperature reached at the conductor. The temperature of the conductor follows a law of the type $P_{opt} \propto T_{CONDUCTOR}^4$, i.e. the optical power of the emitted radiation is proportional to the temperature raised at the power of 4. The wavelength is also in function of the temperature, even though not with the same law. It is possible to directly measure the temperature $T_{CONDUCTOR}$ of the conductor.

However, this is not an easy task: the temperature $T_{CONDUCTOR}$ of the conductor can easily be larger than 900° C., which is not a temperature easily measured or directly controlled (in particular for a MEMS device). Moreover, the transducers that transduce the temperature $T_{CONDUCTOR}$ of the conductor may output voltages which are not easily managed by a microcontroller. This in general requires the use of Zener diodes for saving the microcontroller and static converters (e.g., direct-current/direct-current, DC/DC converters) for reducing the voltages are regularly used.

Techniques for reducing the equipment are therefore pursued.

In addition, there are some issue in the measurements as performed by the detector. In some implementations, the emitter does not send radiations continuously, but in periodic fashion (impulse train). For example, the emissions may follow a squared signal, such that "hot" periods (where the Joule effect causes the temperature to arrive at the temperature necessary for emitting the radiation at a specific wavelength) are alternate to "cold" periods (where no power is provided to the conductor, i.e. no Joule effect is present, and the temperature of the conductor decreases).

However, it has been noted that in this way the measurements are suboptimal. The measurements obtained from the electric signal (e.g., as obtained by the microphone or as subsequently processed) are notwithstanding affected by errors due to thermal phenomena, which render the measurement difficult to be obtained. For example, thermoacoustic waves may be generated, which transfer unwanted heat, which notwithstanding arrives to the detector and introduces errors in the detection.

Techniques for reducing the errors due to thermal phenomena are also pursued.

In particular, it would be preferred to have an emitter which generates radiations without unwanted dependencies on the voltage and on the ambient temperature.

SUMMARY

In accordance to an aspect, there is disclosed an emitter for emitting radiations at a specific wavelength, comprising:
  a Joule-heated emitting electrical conductor, configured to emit radiations at the specific wavelength at an emission temperature,
  a controller configured, in operation, to control a variable voltage subjected to the Joule-heated emitting electrical conductor and modulated according to a duty cycle, the duty cycle being variable between:
  a high-average power duty cycle during hot periods, so that the Joule-heated emitting electrical conductor is subjected to a high-average power to reach and maintain the emission temperature; and a low-average power duty cycle during cold periods alternated to the hot periods, so that the Joule-heated emitting electrical conductor is subjected to a low-average power to reach a temperature smaller than the emission temperature, wherein the low-average power duty cycle is smaller than the high-average power duty cycle, wherein at least one of the high-average power duty cycle and the low-average power duty cycle is defined based on at least one temperature-indicative measured value indicative of the ambient temperature as measured.

Accordingly, it is not necessary to have a sensor directly measuring the temperature of the Joule-heated emitting electrical conductor.

In accordance to an aspect, the controller may define, for at least one hot period, the high-average power duty cycle as the duty cycle that permits to reach and maintain the emission temperature at the Joule-heated emitting electrical conductor.

Hence, negative effects of the change of the ambient temperature are circumvented.

In accordance to an aspect, the controller may define, for at least one hot or cold period, the duty cycle in dependency of:
the at least one temperature-indicative measured value, so that a high ambient temperature is compensated by a low duty cycle, and vice versa.

In accordance to an aspect, the controller may define, for at least one hot or cold period, the duty cycle also in dependency of:
at least one voltage-indicative measured value indicative of the voltage which is applied to the Joule-heated emitting electrical conductor as measured, so that a high voltage is compensated by a small duty cycle, and vice versa.

Hence, the variations in the voltage at the Joule-heated emitting electrical conductor are compensated.

In accordance to an example, the controller (250) may be configured to define, for at least one cold period, the low-average power duty cycle as the duty cycle causing a decrement of electrical power with respect to the high-average power, wherein the decrement is constant irrespective of the ambient temperature.

Accordingly, the sensed value is more reliable and negative effects of thermoacoustic phenomena are compensated.

In accordance to an aspect, during an initialization procedure, the controller may be configured to control a variable voltage subjected to the Joule-heated emitting electrical conductor and modulated according to a duty cycle, the duty cycle being variable between:
a high-average power duty cycle during hot periods, so that the Joule-heated emitting electrical conductor is subjected to a high-average power to reach and maintain the emission temperature; and
a low-average power duty cycle during cold periods alternated to the hot periods, so that the Joule-heated emitting electrical conductor is subjected to a low-average power to reach a temperature smaller than the emission temperature, wherein the low-average power duty cycle is smaller than the high-average power duty cycle,
wherein, during the initialization procedure, the decrement between the high-average power and the low-average power is maintained constant and the ambient temperature is also maintained constant,
wherein the controller is configured, in operation, to define the low-average power duty cycle in such a way that the decrement between the high-average power and the low-average power is the same of the decrement between the high-average power and the low-average power experienced during the initialization procedure.

This may permit to also compensate for negative thermoacoustic phenomena.

In accordance to an aspect, there is provided a sensor for determining characteristics of a fluid, comprising:
an emitter as above, the specific wavelength being a wavelength characteristic of the fluid; and
a detector configured to detect an electric signal associated to the radiation emitted by the emitter,
wherein the emitter and the detector are disposed so that the radiation emitted by the emitter propagates through a target volume containing target fluid, so that the electric signal is associated to the characteristics of the fluid.

The sensor may operate according to an initialization procedure which provides multiple emissions and detections, through the detector, for different known amounts of fluid, so as to individuate a detection law mapping amounts of fluid onto reading units to be converted into amounts of fluids, wherein the sensor is configured, in operation, to define the low-average power duty cycle in such a way that the decrement between the high-average power and the low-average power is the same of the decrement between the high-average power and the low-average power experienced during the initialization procedure.

In accordance to an aspect, there is provided a method for emitting radiations at a specific wavelength, comprising:
through a Joule-heated emitting electrical conductor, emitting radiations at the specific at an emission temperature,
wherein emitting is subjected a modulation according to a duty cycle, the duty cycle being variable between:
a high-average power duty cycle during hot periods, so that the Joule-heated emitting electrical conductor is subjected to a high-average power to reach the emission temperature; and
a low-average power duty cycle during cold periods alternated to the hot periods, so that the Joule-heated emitting electrical conductor is subjected to a low-average power to reach the sub-emission temperature, wherein the low-average power duty cycle is smaller than the high-average power duty cycle,
wherein at least one of the high-average power duty cycle and the low-average power duty cycle is defined based on at least one temperature-indicative measured value indicative of the ambient temperature as measured.

In accordance to an aspect, there is provided a sensing method for determining characteristics of a fluid, comprising:
performing the method above;
permitting a propagation of the radiation through a target volume containing target fluid; and
detecting an electric signal associated to the radiation emitted by the emitter, so that the electric signal is associated to the characteristics of the fluid.

In accordance to an aspect, there is provided a non-transitory storage unit storing instruction which, when running on a computer, cause the computer to perform a method as above.

BRIEF DESCRIPTION OF THE DRAWINGS

FIGS. 4a and 4b shows pulse width modulations, PWMs, associated to an emitter which may be the emitter of FIG. 2;

DETAILED DESCRIPTION OF ILLUSTRATIVE EMBODIMENTS

Throughout the description, reference is prevalently made to "gas", even though it is intended that it is valid for a fluid.

Figure 1A:
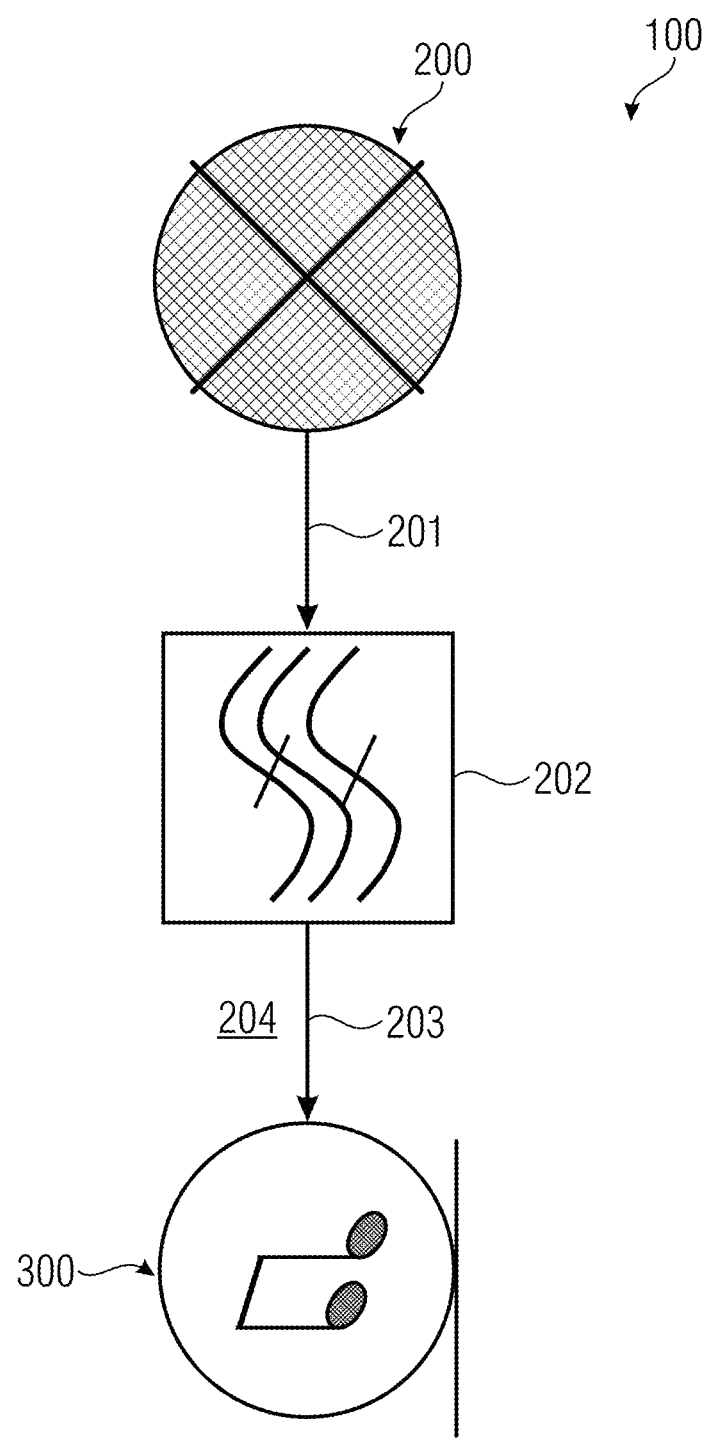
FIGS. 1*a* and 1*b* show two schemes of a fluid sensor(s) according to an example.

FIG. 1a shows a schematized example of fluid sensor 100. The sensor 100 may include an emitter 200 (e.g., optical emitter, light emitter, IR emitter, etc.) and a detector 300 (e.g., optical detector, light detector, IR detector, etc.). The sensor 100 may be, for example, a non-dispersive infrared (NDIR) sensor or a photoacoustical sensor (PAS). The sensor 100, the emitter 200, and the detector 300 may be MEMS devices.

The emitter 200 may emit a radiation 201 at a specific wavelength $\lambda_0$ (which may be chosen to be, for example, the characteristic wavelength of a particular fluid to be measured). The radiation 201 may be or include light. The radiation 201 may be or include infrared (IR) radiation (e.g., MIR radiation). The radiation 201 may include laser radiation. The radiation 201 may be at a specific wavelength $\lambda_0$, in the sense that it is at a narrow band, which includes the particular wavelength $\lambda_0$. The narrowband may be approximated to an interval $[\lambda_0-\delta\lambda, \lambda_0+\delta\lambda]$, with $\delta\lambda$ a small incremental wavelength.

The sensor 100 may include a detector 300 which receives radiation 203 emitted by the emitter 200. The detector 300 may be, for example, a light intensity detector or a photoacoustical detector. If the detector 200 is a photoacoustical detector, it includes a microphone which transduces variations of pressure (acoustic waves, sound) onto electrical signals.

An optical filter 202 may be interposed between the emitter 200 and the detector 300. The optical filter 202 may include a photonic crystal structure. In alternative, the optical filter 202 may be a Fabry-Perot filter. The optical filter 202 may be understood as a wavelength selective structure providing the radiation 203 in an even more restricted narrow band, still containing the specific wavelength $\lambda_0$. E.g., the band becomes $[\lambda_0-d\lambda, \lambda_0+d\lambda]$ with $d\lambda<<\delta\lambda$. It is noted that the optical filter 202 may be considered a part of the emitter 200 even though it is explicitly shown in the schematization of FIG. 1a for clarity.

Accordingly, an optical path 201, 203 is defined between the emitter 200 and the detector 300. In the optical path 201, 203, the radiation 203 passes through a target volume 204 (target environment) in which a target gas (or more in general a target fluid) is present. The target gas absorbs and emits photons at a specific wavelength (each gas being characterized by a specific wavelength, which is the wavelength 201 or 203 which is intended to be transmitted by the emitter 200). Accordingly, the radiation 203, after having propagated through the target volume 204 (and after having excited the molecules or atoms of a specific gas of which it is intended to measure the amount or concentration), is used for determining the properties of the fluid, e.g. by measuring its quantity or concentration of the gas. In particular, electrical signals may be processed at the decoder, the electrical signal being indicative of the radiation reaching the detector 300.

In some examples, the detector 300 is enclosed in a sealed volume in which a reference gas is present, hence permitting to measure the quantity or concentration of the target gas placed (in the target volume 204) outside the closed volume. In other examples, the target gas directly arrives inside the detector 300, and its amount or concentration is directly measured by the detector 300.

Figure 1B:
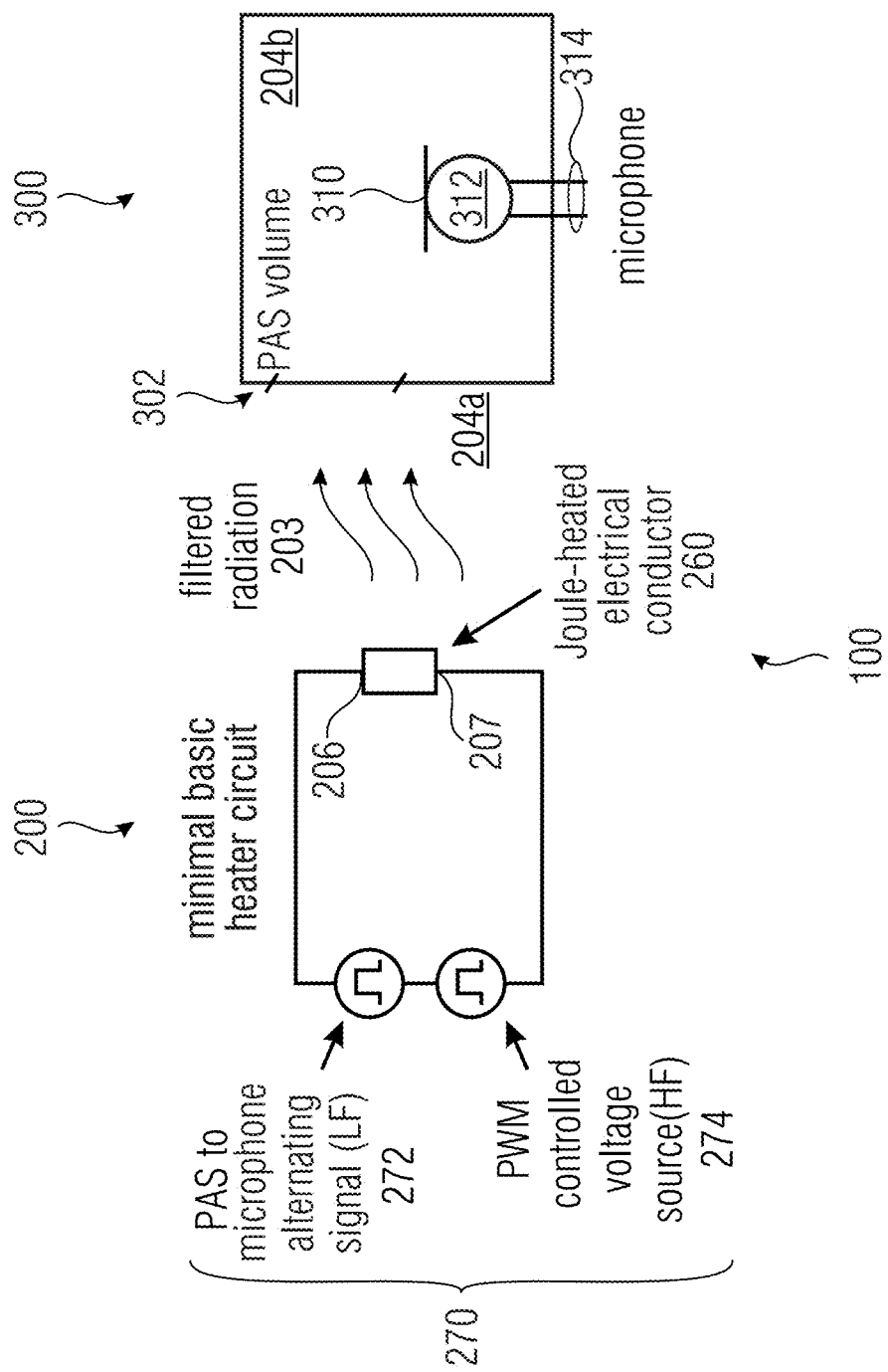
Figure 2:
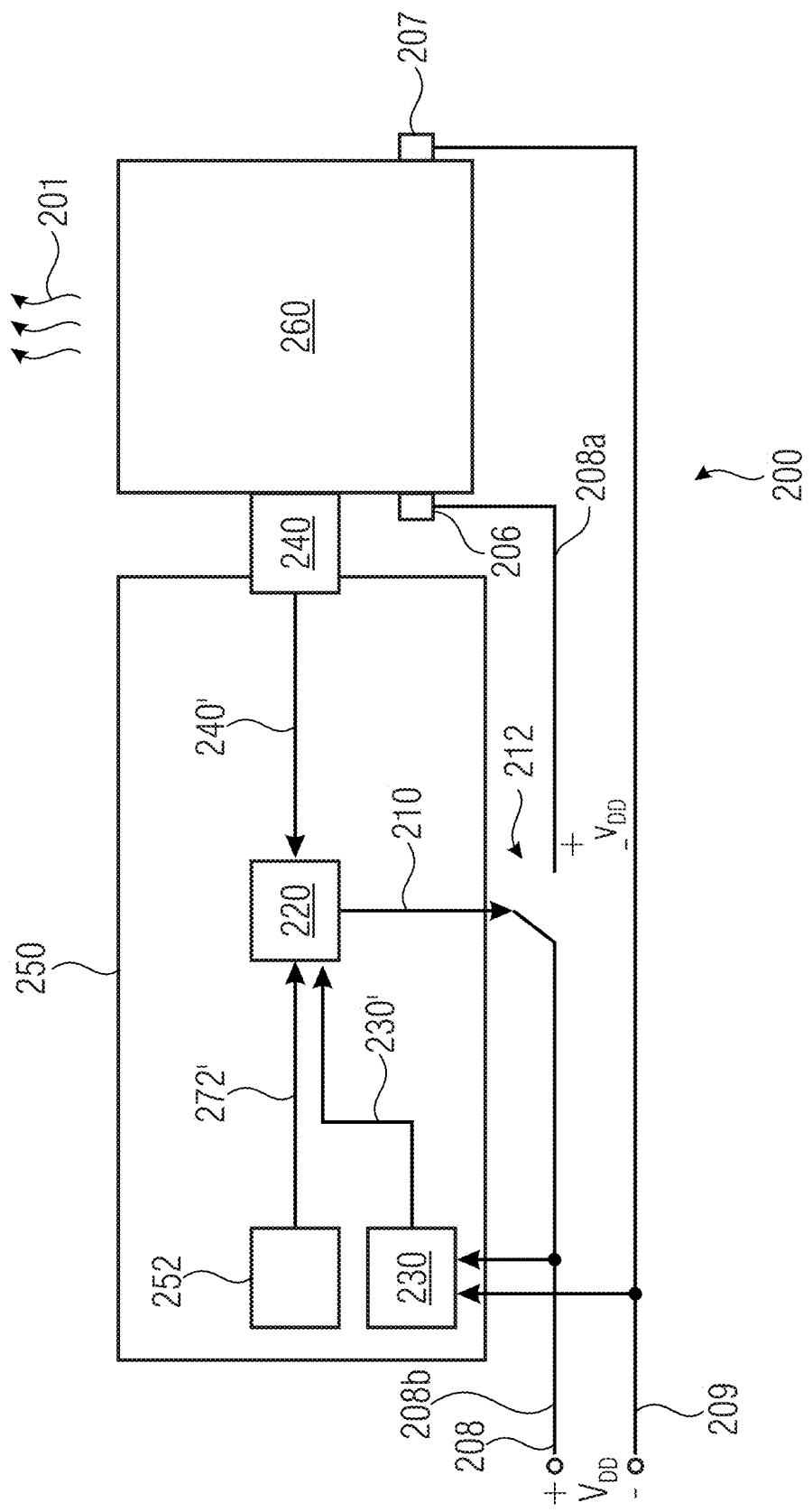
FIG. 2 shows an emitter which may be the emitter shown in FIG. 1a or 1b.

Another schematic drawing of sensor 100 (which may the same of FIG. 1a) is shown in FIG. 1b (reference can also be made to FIG. 2). The sensor 100 includes a Joule-heated emitting electrical conductor (heater) 260. The joule-heated emitting electrical conductor 260 may be of the type having a suspended heating membrane anchored to sustaining elements. The heating membrane may be heated by Joule effect. By virtue of its temperature, the joule-heated emitting electrical conductor 260 generates radiations according to the Planck's law (the hotter the heater 260, the smaller the wavelength $\lambda_0$).

The Joule-heated emitting electrical conductor (heater) 260 may be heated by Joule effect at a temperature that causes the emission of the radiation 201 at the wavelength $\lambda_0$ (or its filtered version 203, the optical filter 202 not being shown). After having propagated through the target volume 204a (which is replenished of target gas to be measured) the optical radiation reaches a sealed volume (e.g., PAS volume) 204b. The sealed volume 204b contains a fixed known amount of a reference gas. The radiation excites the molecules or atoms of the target gas in the target volume 204a and the reference gas in the sealed volume 204b. Radiation 203 passes through a transparent window 302 and the sealed volume 204b, and causes a modification of the temperature within the sealed volume 204b, which in turn modifies the pressure and causes a membrane 310 of a microphone 312 to be deformed accordingly. An electric signal 314 may therefore be generated. The electric signal 314 may provide information regarding the amount or concentration of the target gas in the target volume 204a.

The PAS detector may be substituted by a detector which directly converts the radiation entering through the window 302 into an electrical signal and in that case, there would be no microphone 312 and no membrane 310, but in any case, an electric signal indicative of the quantity of the target gas would be notwithstanding obtained. It is also to be noted that, in any case, it is not necessary that the volume of the detector 300 is closed, but it is also possible to have an open volume sensor, without reference gas inserted in a closed volume.

As can be seen from FIG. 1b, the Joule-heated emitted electrical conductor 260 may be structurally and constructively made so that:

at an emission temperature $T_{HOT}$ (e.g. 950° C. or other temperatures over 400° C. or over 600° C.) the Joule-heated emitting electrical conductor 260 emits radiation including a specific wavelength $\lambda_0$ (which may be the wavelength characteristic of a particular gas to be measured);

at at least a sub-emission temperature $T_{COLD}$ (e.g., 85° C.), e.g. with $T_{COLD}<<T_{HOT}$ (e.g. with sub-emission temperature $T_{COLD}$ being equal to or greater than the ambient temperature $T_{AMBIENT}$, e.g. $T_{COLD}>T_{AMBIENT}$) the Joule-heated emitting electrical conductor 260 does not emit (or emits in negligible amount of) radiation at the specific wavelength $\lambda_0$ (it could irradiate at a different band following the Planck's law) or it could irradiate it for a negligible amount.

It is noted that, following the Planck's law, at the sub-emission temperature $T_{COLD}$ some negligible emission at the wavelength $\lambda_0$ could notwithstanding be caused. For example, the radiation intensity may be reduced to less than 5% or even less than 1% or less than 0.1% at the sub-emission temperature $T_{COLD}$. Here, when referring to the sub-emission temperature, it is imagined that the amount of emission at the wavelength $\lambda_0$ is negligible and is approximated to 0. Notably, when referring to sub-emission temperature ($T_{COLD}$), reference can be made to a range of sub-emission temperatures (e.g. $T_{AMBIENT} \leq T_{COLD} \leq T_{COLD,MAX} < T_{HOT}$).

It is also to be noted that the sub-emission temperature $T_{COLD}$ is not necessarily one single pre-defined temperature value. A range of sub-emission temperatures may therefore be defined (i.e., the range of temperatures at which the radiation at the wavelength $\lambda_0$ is not generated or is negligible). Therefore, in subsequent passages, reference is prevalently made to "a sub-emission temperature" to indicate that the sub-emission temperature is not necessarily at one single temperature value.

To the contrary, as will be shown below, the emission temperature $T_{HOT}$ (which, for a particular gas, may be ideally one single value) can be controlled with high accuracy by relaying on techniques discussed below. Therefore, in subsequent passages, reference is prevalently made to "the emission temperature $T_{HOT}$", in the sense that it is intended to reach a particular emission temperature value.

In particular, emission at the Joule-heated emitting electrical conductor 260 may be controlled so that:

during some periods (e.g., "hot periods") the radiation 201, 203 at the wavelength $\lambda_0$ is actually emitted, in a substantial amount, by the Joule-heated emitting electrical conductor 260, and during other periods ("cold periods") alternated to the hot periods, the Joule-heated emitting electrical conductor 260 remains at a sub-emission temperature $T_{COLD}$ (e.g., below the emission temperature $T_{HOT}$) at which the radiation does not include the specific wavelength $\lambda_0$ or includes it in a negligible amount.

The variable voltage $v_{DD}$ (see also FIGS. 2 and 4) at the Joule-heated emitting electrical conductor 260 is here also indicated as a signal 270. The signal 270 may be the understood as combining the effects of the following two signals:

a low frequency (LF) signal 272 (indicated in FIG. 1b as "PAS to microphone alternating signal", but which can also operate with non-PAS equipment);

a high frequency (HF) signal 274 (indicated in FIG. 1b as "PWM controlled voltage source").

The signals 272 and 274 may be understood as PWM signals, and the resulting signal 270 may understood as the combination of the modulations of the two PWM signals 272 and 274. An impulse train is therefore generated. As it will be explained later, the signals 272 and 274, modulated one inside another, cause the Joule-heated electrical conductor 260 to operate according to two different modes:

a high-average power mode, during the hot periods, in which the Joule-heated emitting electrical conductor 260 is subjected to a high-average power, reaching and maintaining the emission temperature $T_{HOT}$; and a low-average power mode, during the cold periods, in which the Joule-heated emitting electrical conductor 260 is subjected to a low-average power, reaching and maintaining a sub-emission temperature $T_{COLD}$ (the low-average power smaller than the high-average power).

As will be shown later, the HF signal 274 is responsible for reaching and maintaining the emission temperature $T_{HOT}$ during the hot periods and to be maintained at a sub-emission temperature (smaller than the emission temperature $T_{HOT}$) during the cold periods. The LF signal 272 is responsible for timing the alternation of the hot periods with the cold periods.

In some examples, the LF signal 272 may be a two-state periodic signal divided into two semi-periods, each semi-period having the time length of one half of the period of signal 272. FIG. 4 shows that a period 472 of the LF signal 272 is being divided into two semi-periods 472h (i.e. hot periods) and 472c (i.e. the cold periods). It is to be noted, however, that it is not necessary that the period 472 is exactly divided into two semi-periods of equal length, but different subdivisions are possible. In general terms, it may be understood that the period 472 is subdivided among hot sub-periods 472h (i.e., the hot periods) and cold sub-periods 472c (i.e., the cold periods), with reciprocal lengths which are variable according to the particular implementation.

The LF signal 272 may have a frequency between 10 Hz and 40 Hz or 100 Hz (e.g., 25 Hz). This frequency is appropriated for permitting the transmission of pulses of radiations at the specific wavelength $\lambda_0$ (during the hot periods) alternated to the absence (during the cold periods) of radiations at the wavelength $\lambda_0$. The frequency range between 10 Hz and 40 Hz or 100 Hz is particularly appropriated for permitting an effective detection at the detector 300 (e.g., when the detector 300 is a photoacoustic detector, the microphone 312 may reliably detect sound in the range between 10 Hz and 40 Hz or 100 Hz).

The HF signal 274 may be understood, for example, as a digitally controlled PWM, which modulates the voltage of the Joule-heated emitting electrical conductor 260 between:

a high voltage value $V_{DD}$ (where the magnitude of the voltage is greater than 0, e.g. greater than 5V or greater than 12V in other cases, e.g. $V_{DD}$=12V); and a 0 voltage or low voltage value (where the magnitude of the voltage is smaller than the magnitude of the high voltage value).

The PWM of the HF signal 274 has a high duty-cycle in the hot periods 472h (thus providing high average power to the Joule-heated emitting electrical conductor 260), and a low duty-cycle in the cold periods 472c, so as to reduce the average power provided to the Joule-heated emitting electrical conductor 260. The duty cycle for a PWM is in general an a dimensional, positive number (or a percentage) comprised between 0 and 1 (or 0% and 100%). The duty cycle indicates the relative proportions between the time length of the high voltage value and the time length of the 0 voltage or low voltage value in a particular whole period: e.g., if the duty cycle is 0, the high voltage value is never achieved; if the duty cycle is 1 (or 100%), the high voltage value is continuously applied; if the duty cycle is 0.5 (or 50%), both the high voltage value and the 0 voltage or low voltage value are alternated for the same time length, and the average voltage applied to the heater 260 is $V_{DD}/2$. In this case, however, the high duty-cycle in the hot periods 472h is defined so as to reach the emission temperature.

FIG. 2 shows an example 200 of an emitter (e.g., the emitter of FIGS. 1a and/or 1b). The emitter 200 includes the Joule-heated emitting electrical conductor (heater) 260 as the element generating the radiation 201 under the effect of a variable voltage $v_{DD}$. The voltage $V_{DD}$ (signal 270) may be fed to terminals 206 and 207 of the Joule-heated emitting electrical conductor 260 under a control 210 exerted by a controller 250. The terminals 206 and 207 may be connected to conductor lines 208 and 209, respectively. Line 209 may be imagined as at mass, and line 208 may be fed by a constant potential $V_{DD}$>0 (or lines 208 and 209 are simply at different polarities or potentials). A switch 212 may separate a proximal branch 208b (at the constant potential $V_{DD}$>0) and a distal branch 208a (connected to the terminal 206), hence causing the alternance between $V_{DD}$ and 0. The variable voltage $v_{DD}$ may be provided to the Joule-heated emitting electrical conductor 260 as pulses of fixed voltage amplitude $V_{DD}$ controlled by the switch 212 controlled by the controller 250. (In alternative embodiments, different solutions can be used. In some cases, the variable voltage $v_{DD}$ could be directly provided by the controller 250). The switch 212 may be, for example, a metal-oxide-semiconductor field-effect transistor, MOSFET, and the control 210 may be connected to the gate of the MOSFET, while the terminals associated to the switch 212 may be the source and the drain of the MOSFET (one of the source and the drain being connected to the distal branch 208a, and the other one being connected to the proximal branch 206).

The control 210 may be understood as controlling the PWMs of the signals 272 and 274. The controller 250 may include or be connected in input to a timer 252, which provides a timing signal 272' controlling the LF signal 272: the timing signal 272' may control the transitioning from a hot period to a cold period and vice versa. The timer 252 may be or include a phased locked loop, PLL, circuit and/or may be fed by an external clock input (not shown).

The emitter 200 may include, or be connected in input to, a voltage sensor 230 (which, in FIG. 2 is shown as an internal to the controller 250, but it can also be an external component). The voltage sensor 230 may be connected to the lines 208 and 209 (e.g., the branch 208a and the line 209) which feed the terminals 206 and 207 of the Joule-heated emitting electrical conductor 260 (in particular, when the switch 212 is present, the portion of terminal 208, is placed downstream to the switch 212). In examples, the voltage sensor 230 may be connected to only one of the two conductor lines 208 and 209 (e.g., when the line 209 is already connected to the mass, it may be not necessary to also connect the voltage sensor 230 directly to the conductor line 209, by virtue that also the voltage sensor 230 may be connected to the mass). In examples, the voltage sensor 230 may be substituted by another electric sensor (e.g., current sensor) which provides a measurement associated to the voltage. In any case, the voltage sensor 230 provides at least a voltage-indicative measured value 230', which gives information on the actual voltage experienced by the Joule-heated emitting electrical conductor 260. The voltage-indicative measured value 230' may be in the digital domain, for example. It has been noted that, even with the extremely precise control of the variable voltage $v_{DD}$ and/or of the switch 212, some unwanted variations of voltage can, notwithstanding, appear. Therefore, by sensing the voltage $v_{DD}$ actually provided to the Joule-heated emitting electrical conductor 260, it is possible to obtain a more efficient control.

It has been understood that it is not necessary to measure the input voltage $V_{DD}$ in real time. It is possible to measure the input voltage $V_{DD}$ before subjecting the Joule-heated emitting electrical conductor 260 with the variable voltage $v_{DD}$.

The emitter 200 may include a temperature sensor 240 (which, in this case, is shown as being part of the controller 250, but can also be provided as a separate element). The temperature sensor 240 may provide a temperature-indicative measured value 240' (e.g., in the digital domain), which is indicative of the ambient temperature $T_{AMBIENT}$.

It has been understood that the ambient temperature $T_{AMBIENT}$ may be measured as the initial temperature of the Joule-heated emitting electrical conductor 260 when the Joule-heated emitting electrical conductor 260 is in thermal equilibrium with the environment. Therefore, the ambient temperature $T_{AMBIENT}$ may be simply obtained by measuring the temperature of the Joule-heated emitting electrical conductor 260 before the start of subjecting the Joule-heated emitting electrical conductor 260 with the variable voltage $v_{DD}$. Hence, the measurement of the ambient temperature $T_{AMBIENT}$ does not require the presence of an additional temperature sensor which somehow "senses the environment temperature". Rather, the temperature sensor 240 may simply be applied directly to the Joule-heated emitting electrical conductor 260. It is may be simply provided that the Joule-heated emitting electrical conductor 260 is switched off for a pre-defined amount of time which sufficient to reach the thermal equilibrium with the environment. Basically, the reading of the temperature-indicative measured value 240' may temporally precede the process of subjecting the heater 260 with the variable voltage and the consequent process of emitting the radiations at the wavelength $\lambda_0$. Notably, instead to $T_{AMBIENT}$, reference could simply be made to $T_{CONDUCTOR, INITIAL}$.

The controller 250 may include a PWM controller (duty-cycle definer) 220, which may be input by any of the voltage-indicative measured value 230', temperature-indicative measured value 240', and a timing signal 272'. Accordingly, the controller 250 may define the duty-cycle for the hot periods and the duty-cycle for the cold periods, and determine the transitions between the hot periods and the cold periods (and vice versa), by exerting the control 210 (on the basis of at least one of the timing signal 272', voltage-indicative measured value 230' and temperature-indicative measured value 240'), according to the specific implementation for the voltage control.

It is to be noted, however, that the control 210 is not necessarily established in real time: simply, the input voltage $V_{DD}$ and the ambient temperature $T_{AMBIENT}$ may be measured before starting to feed the Joule-heated emitting electrical conductor 260 with the variable voltage $v_{DD}$. Hence, before starting the impulse train, the high duty-cycle and the low duty-cycle are defined and do not change during the emission.

In some examples, the voltage is controlled in real time.

The controller 250 may have a chip structure, and all or at least part of its elements may be provided inside of one single structure (e.g., a package structure). At least one of the timer 252, voltage sensor 230, and temperature sensor 240 may be internal to the chip structure or external to it.

The controller 250 may also be the element that controls the operations of the detector 300 and, more in general, the operations of the sensor 100. The controller 250 may include a PWM controller 220, which is here shown as driving the control 210.

FIG. 4a shows a graph showing the variable voltage $v_{DD}$ (signal 270) in time. Scheme (b) is a magnified scheme of portion 402.

As can be seen, the variable voltage $v_{DD}$ is defined, according to a variable duty cycle, as being between the value 0 (or another low-voltage value) and $V_{DD}$.

FIG. 4a shows a sequence, having period 472, of the LF signal 272. Each period 472 is, in turn, subdivided into different sub-periods:

- at least one sub-period 472h, which corresponds to a hot period; and
- at least one sub-period 472c, which corresponds to a cold period.

(As explained above, FIG. 4a shows the sub-periods 472h and 472c being two semi-periods of exactly same length, but this is not general, and different lengths and different subdivisions are possible).

The subdivision of the LF signal 272 in consecutive periods 472 may be controlled, for example, by the timing signal 272' e.g., based on the timer 252.

As can be seen from FIG. 4a, the hot periods 472h and the cold periods 472c are characterized by different duty cycles: while in the hot periods 472h the duty cycle is high, in the cold periods 472c the duty cycle is low.

Accordingly, in the hot periods 472h, a high-average power is provided to the electrical conductor 260, while a low average power (greater than 0) is provided to the electrical conductor 260 in the cold periods 472c. The duty cycle in the hot periods 472h causes the temperature of the Joule-heated emitting electrical conductor 260 to reach the emission temperature at which the radiation at the intended wavelength λ is generated. On the other side, it has been understood that also the low average power may be defined in such a way to reach a constant decrement of the average power in the cold periods 472c with respect to the average power in the hot periods 472h (the constant decrement does not change with the ambient temperature).

FIG. 4b shows the duty cycle during a hot period 472h. (An analogous graph would be obtained for the cold periods 472c, apart from the fact that the reciprocal durations of the slots would be different). As shown in scheme (b), the variable voltage $v_{DD}$ may take, during high voltage slots 474h, the high voltage value $V_{DD}$, while for low voltage slots 474b the variable voltage $v_{DD}$ may take the value 0 (or another low voltage value). The relative duration of the slots 474h and 474b is determined by the duty cycle (e.g., as defined by the PWM controller 220). The duty cycle is based on a $time_{period}$ indicated with 474, which is much smaller than the thermal time constant $\tau_{thermal}$. FIG. 4b shows a more elongated extension of the high voltage slot 472h with respect to the low voltage slot 474b, and this is expectable as scheme (b) relates to a hot period 472h. In the cold period 472c, the duration of slot 474h would be much shorter and the duration of the slot 474b would be much longer.

As explained above, the duty cycle may be defined by the controller 250 (and in particular by the PWM controller 220) on the basis of at least one of the voltage-indicative measured value 230' and the temperature-indicative measured value 240'. The time variation 480 of the high voltage slots 474h may be modified, for example, in accordance to the particular voltage control that is implemented.

Figure 3:
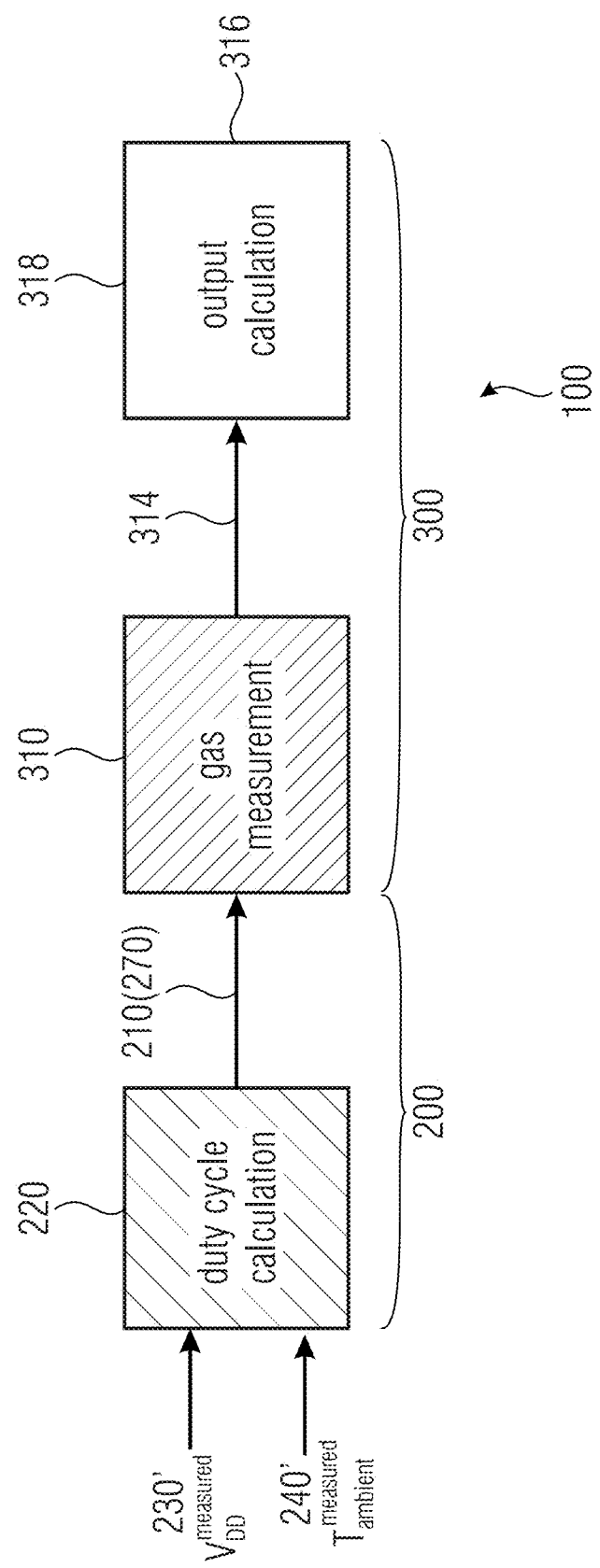
FIG. 3 shows a scheme of a fluid sensor which may the fluid sensor of FIG. 1a or 1b.

FIG. 3 shows an example scheme of the sensor 100 with simplified operational blocks (which may be understood as both, elements of the sensor 100 and as method steps). At the side of the emitter 200, a duty cycle calculation block 220 (which may be understood as corresponding to the PWM controller 220), may have, in input, the voltage-indicative measured value 230' ($V_{DD}^{measured}$) and the temperature-indicative measured value 240' ($T_{AMBIENT}^{measured}$). The PWM controller 220 may output a control 210 (intended for controlling the signal 270) for subjecting the Joule-heated emitting electrical conductor 260 to the variable voltage $v_{DD}$.

At the detector 300, a gas (or fluid) measurement block 310 may be provided. When the detector 300 is obtained based on the photoacoustic sensing (e.g., it comprises the microphone 312), a vibration of the membrane is caused converted into an electric signal 314. The signal 314, in its original analog version of in a digital version, may be provided to an output calculation block 318.

The final measured value 316 (e.g., concentration and/or quantity of the fluid) may be output (e.g., provided to a display peripheral or otherwise signaled to a user, and/or transmitted or stored in a storage memory, such as a flash memory or a register) by the output calculation block 318 as a final measurement value (or more in general, as characteristic of the fluid).

Figure 5A:
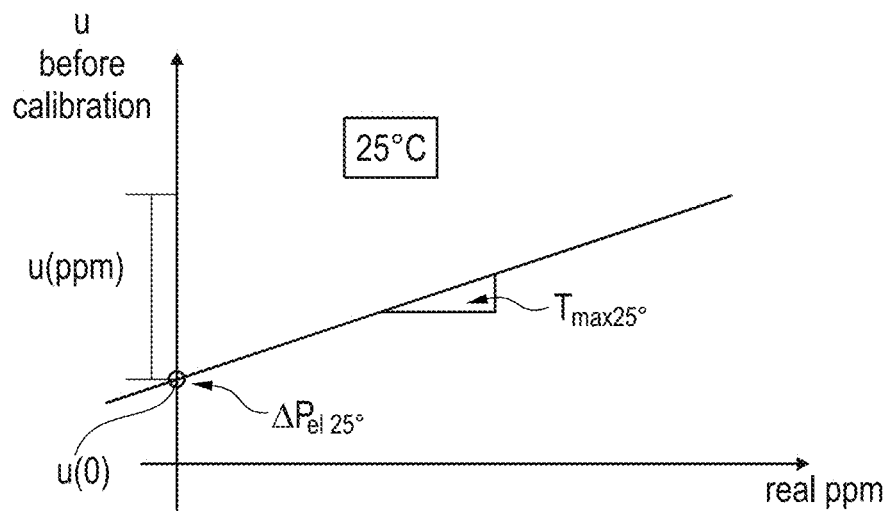
FIGS. 5a, 5b, 5c, and 5d are graphs showing advantages of the present techniques according to embodiments.

The emitter 100 (and the sensor 200, as well) may have, at block 318, the knowledge of a relationship between the electric signal 314 and the real amount of the gas (or fluid), e.g. in ppm (parts per million). An example in provided in the graph of FIG. 5a, showing in ordinate a reading unit u (obtained from the signal 314) and in abscissa the real ppm amount of gas (to be output as value 316). It has been understood that the real amount of gas and the signal 314 (value u) are bound to each other through a linear function (linear detection law), which is shown in the graph of FIG. 5a in terms of u=u(ppm)+u(0), where u(ppm) is the expected measurement (proportional to the gas amount), and u(0) is an unwanted offset associated to the temperature.

The slope of the linear function u=u(ppm)+u(0) is associated to the ambient temperature: hence, different ambient temperatures will in principle cause different functions with different slopes. This result can be seen by comparing, the graph of FIG. 5a ($T_{AMBIENT}$=25° C.) and the graph of FIG. 5b ($T_{AMBIENT}$=50° C.). Hence, in principle, a signal 314 as collected by the sensor 200, could result in an incorrect measurement.

The graph of FIG. 5a also shows an offset u(0) in the linear function. Also, in this case, the offset may in principle vary in different measurements. Besides the intended irradiation at the specific wavelength $\lambda_0$, other unwanted thermal phenomena (e.g., thermoacoustic waves) have been observed. These unwanted phenomena may in principle change the offset u(0), thus causing a different reading at block 318 and a misrepresentation of the amount of gas.

However, the present techniques permit to cope with these inconveniences. Here below an exhaustive explanation is provided.

In general terms, the temperature of the conductor 260 (heater) is $T_{CONDUCTOR}=T_{AMBIENT}+\Delta T$ (which, in the hot periods 472h, becomes $T_{HOT}=T_{AMBIENT}+\Delta T_{HOT}$), where $\Delta T$ is the increment of temperature due to the electric power $P_{el}$ provided to the Joule-heated emitting electrical conductor 260. The general formula $T_{CONDUCTOR}=T_{AMBIENT}+\Delta T$ becomes $T_{HOT}=T_{AMBIENT}+\Delta T_{HOT}$ in the hot periods 472h, and $T_{COLD}=T_{AMBIENT}+\Delta T_{COLD}$ in the cold periods (notably, $T_{COLD}$ is not necessarily pre-defined, and simply need to be a sub-emission temperature which generates a null or negligible amount of radiation at the wavelength $\lambda_0$). If $T_{AMBIENT}$=25° C. and the emission temperature required for emitting radiation at a specific wavelength λ is $T_{HOT}$=950° C., then during a generic hot period 472h the electric power $P_{el,HOT}$ shall provide an increment of temperature which is $\Delta T_{HOT}=T_{HOT}-T_{AMBIENT}$=950° C.-25° C.=925° C.

During a generic hot period 472h, the electric average power $P_{el,HOT}$ is conditioned by the high-average power duty cycle $D_{HOT}$ (e.g., the length of the slot 474h divided by the length of $time_{period}$), and may be the average of the power along the length of $\text{time}_{period}$ 474. In practice, the electric power $P_{el,HOT}$ may be expressed as an average power expressed by $$P_{el,HOT} = D_{HOTR} \cdot \frac{V_{dd}^2}{R_{el,HOT}}$$

where $V_{dd}$ is the high voltage value provided to the terminals 206 and 207 of the Joule-heated emitting electrical conductor 260, and $R_{el,HOT}$ is the electrical resistance [Ω] of the Joule-heated emitting electrical conductor 260 (the electrical resistance $R_{el}$ in general varies with the temperature, and this may be mirrored by assuming that the resistance in the hot periods is different from the resistance in the cold periods, i.e. $R_{el,HOT} \neq R_{el,COLD}$).

It has indeed been noted that, in general, the increment in temperature ΔT is proportional to the average power $P_{el}$ with a proportionality coefficient which is the thermal resistance $$R_{th}\left[\frac{°C}{W}\right],$$

which is the same as $$\frac{K}{W}\bigg].$$

This provides $$\Delta T = R_{th} \cdot D \cdot \frac{V_{dd}^2}{R_{el}}$$

(with D generic duty cycle, $R_{th}$ generic thermal resistance, $R_{el}$ generic electrical resistance, $V_{dd}$ constant high-voltage value) which, in a generic hot period 472h, becomes $$\Delta T_{HOT} = R_{th,HOT} \cdot D_{HOT} \cdot \frac{V_{dd}^2}{R_{el,HOT}}.$$

Putting together the results above, it follows that the temperature of the Joule-heated emitting electrical conductor 260 obeys to the rule:

$$T_{CONDUCTOR} = T_{AMBIENT} + R_{th} \cdot D \cdot \frac{V_{DD}^2}{R_{el}}$$

which, in the generic hot period 472h, becomes $$T_{HOT} = T_{AMBIENT} + R_{th,HOT} \cdot D_{HOT} \cdot \frac{V_{DD}^2}{R_{el,HOT}}.$$

One could imagine that, in order to define the high-average power duty cycle $D_{HOT}$, the temperature of the Joule-heated emitting electrical conductor 260 should be sensed in real time. However, it has been understood that this is not necessary.

In fact, it has been understood that, instead of the temperature of the Joule-heated emitting electrical conductor 260, it is possible to detect the ambient temperature $T_{AMBIENT}^{measured}$ (or another temperature-indicative measured value 240') and the actual voltage $V_{DD}^{measured}$ (or another voltage-indicative measured value 230') which is experienced at the terminals 206 and 207 of the Joule-heated emitting electrical conductor 260. It has been understood that, from $$T_{HOT} = T_{AMBIENT} + R_{th,HOT} \cdot D_{HOT} \cdot \frac{V_{DD}^2}{R_{el,HOT}},$$

the duty cycle $D_{HOT}$ can be easily obtained. In fact:
$T_{HOT}$ is the temperature that it is intended to achieve (emission temperature for obtaining the radiation at the wavelength $\lambda_0$), and is therefore known;
$T_{AMBIENT}$ can be $T_{AMBIENT}^{measured}$, obtained by measurement (e.g., through the temperature-indicative measured value 240');
$V_{DD}$ can be $V_{DD}^{measured}$, i.e. the voltage at terminals 206 and 207 of the Joule-heated emitting electrical conductor 260, as obtained by measurement (e.g., through the temperature-indicative measured value 240');
$R_{el,HOT}$ and $R_{th,HOT}$ are respectively the electric resistance of the Joule-heated emitting electrical conductor 260 and the thermal resistance of the Joule-heated emitting electrical conductor 260 in the hot periods (in general, both the electric resistance and the thermal resistance vary according to the temperature, i.e. $R_{el,HOT} \neq R_{el,COLD}$ and $R_{th,HOT} \neq R_{th,COLD}$ but are however both known).

The controller 250 (and in particular the duty-cycle definer 220) may therefore calculate $D_{HOT}$, so as to provide to the Joule-heated emitting electrical conductor 260 with the power necessary for emitting, during the hot periods 472h, the radiation at the wavelength $\lambda_0$.

Hence, in the hot periods 472h, the high-average power duty cycle $D_{HOT}$ may be controlled on the basis of the required emission temperature $T_{HOT}$, at least one voltage-indicative measured value (230') and at least one temperature-indicative measured value (240') as acquired measurements, so as to define the duty cycle necessary to reach maintain the emission temperature.

As explained below, in examples the at least one voltage-indicative measured value (230') and at least one temperature-indicative measured value (240') may be obtained before start of the provision of the voltage to the Joule-heated emitting electrical conductor 260, and the value of the high-average power duty cycle $D_{HOT}$ may therefore be calculated in advance, and maintained subsequently, without further adjustments in real time. Hence, for a complete session of measurements, $D_{HOT}$ may remain constant.

Therefore, during the hot periods 472h, a compensation of the ambient temperature $T_{AMBIENT}$ may be performed: irrespective of the value of $T_{AMBIENT}$, the intended emission temperature $T_{HOT}$ will be reached and maintained. Analogously, a compensation of $V_{DD}$ may be performed: the intended emission temperature $T_{HOT}$ will be reached and maintained.

During the cold periods 472c, radiation at the wavelength $\lambda_0$ is not to be emitted by the Joule-heated emitting electrical conductor 260 (or at least should be emitted in a negligible amount). Hence, in the cold periods 472c the duty cycle $D_{COLD}$ shall be reduced, so as to reduce the average power ($P_{el,COLD}$) provided to the Joule-heated emitting electrical conductor 260, to reduce the temperature and ideally up to avoid the emission.

It has been understood that it is preferable, during the cold periods 472c, to continue to feed the Joule-heated emitting electrical conductor 260 with an amount of low-average power $P_{el,COLD}$ having an offset (decrement) $\Delta P_{el}$, in respect to the high-average power $P_{el,HOT}$, which is constant for all the measurements and does not change in respect to the ambient temperature. Hence, during the cold periods 472c:

$$\Delta P_{el} = P_{el,HOT} - P_{el,COLD} = \text{constant} > 0.$$

In accordance with examples of the present technique, the constant $\Delta P_{el}$ may be defined for example during an initialization (calibration) process 610 (discussed below). It has been noted, in fact, that by keeping always the same constant decrement $\Delta P_{el}$, the offset u(0) in FIGS. 5a, 5b, 5c, and 5d does not change for different measurements, even if taken at different ambient temperatures. Accordingly, during the cold periods 472c the heat transfer caused by the thermoacoustic waves is compensated.

Accordingly, the decrement of power $\Delta P_{el}$ in the cold periods in response to the hot periods is fixed. This effect pre-compensates a possible offset in reading the u(0), which is accordingly known and does not need to be compensated a posteriori.

It is now explained how to define the low-average power duty cycle $D_{COLD}$ to be used in the cold periods 472c. Most of the explanations follow those carried out for the hot periods (see above).

During a generic cold period 472c, the electric low average power $P_{el,COLD}$ is conditioned by the low-average power duty cycle $D_{COLD}$. The electric power $P_{el,COLD}$ may be expressed as an average power expressed by $$P_{el,COLD} = D_{COLD} \cdot \frac{V_{dd}^2}{R_{el,COLD}}$$

where $V_{dd}$ is the (constant) high voltage value provided to the terminals 206 and 207 of the Joule-heated emitting electrical conductor 260 in the cold periods 472h, and $R_{el,COLD}$ is the electrical resistance of the Joule-heated emitting electrical conductor 260 at a sub-emission temperature.

It is known that $$\Delta T_{COLD} = T_{COLD} - T_{AMBIENT} = R_{th,COLD} \cdot D_{COLD} \cdot \frac{V_{dd}^2}{R_{el,COLD}}.$$

Putting together the results above, it follows that the temperature in the cold periods 472c is $$T_{COLD} = T_{AMBIENT} + R_{th,COLD} \cdot D_{COLD} \cdot \frac{V_{DD}^2}{R_{el,COLD}}.$$

$T_{COLD}$ may vary during a generic cold period, since it is not necessary to have a constant $T_{COLD}$.

Here, it is:

$T_{COLD}$ is the (non-necessarily constant) sub-emission temperature (it could be 85° C., for example, for at least one instant in the cold period);

$T_{AMBIENT}$ can be $T_{AMBIENT}^{measured}$, obtained by measurement (e.g. through the temperature-indicative measured value 240');

$V_{DD}$ can be $V_{DD}^{measured}$, i.e. the voltage at terminals 206 and 207 of the Joule-heated emitting electrical conductor 260, as obtained by measurement (e.g. through the temperature-indicative measured value 240');

$R_{el,COLD}$ and $R_{th,COLD}$ are respectively the electric resistance of the Joule-heated emitting electrical conductor 260 and the thermal resistance of the Joule-heated emitting electrical conductor 260.

As explained below, in examples the at least one voltage-indicative measured value (230') and at least one temperature-indicative measured value (240') may be obtained before start of the provision of the voltage to the Joule-heated emitting electrical conductor 260, and the value of the low-average power duty cycle $D_{COLD}$ may therefore be calculated in advance (e.g., together with the calculation of the high-average power duty cycle $D_{HOT}$), and maintained subsequently, without further adjustments in real time. Hence, for a complete session of measurements, $D_{COLD}$ may remain constant.

In the cold periods it is not necessary to reach a particular temperature, but simply to avoid (or render negligible) the emission at the specific wavelength $\lambda_0$. However, as it will be explained later, notwithstanding a control may be performed so that the decrement $\Delta P_{el}$ of the power form the hot periods to the cold periods remains constant, irrespective of the ambient temperature and/or the input voltage $V_{DD}$.

Figure 6:
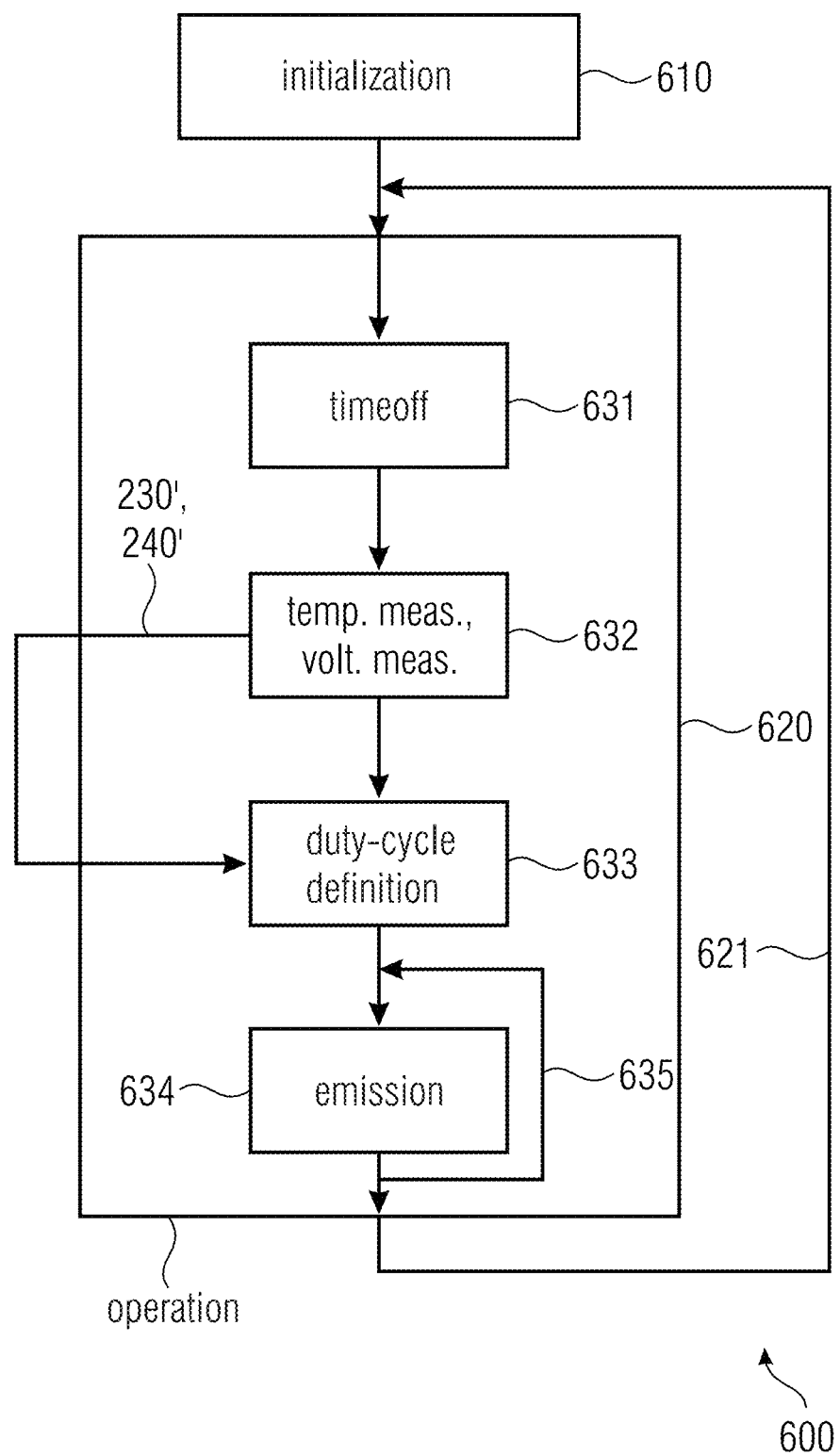
FIG. 6 shows a method according to an example.

FIG. 6 shows method 600 for explaining a way according to which the emitter 100 may operate (the operations specific of the detector 200 are not shown).

At step 610 an original initialization is performed. Subsequently, measurement operations are performed at 620 (iteration 621 refers to the fact that multiple measurements may rely on the same initialization 610).

During the initialization 610, the emitter 100 (and the sensor 300 in general) operates as above (e.g., by generating impulse trains according the duty cycles as above and emitting radiations in hot periods and cold periods as above). Any of the operations 631-634 (discussed below) may therefore be performed during the initialization 610. It is only requested that multiple known amounts of fluid are measured at the same ambient temperature and at the same constant decrement $\Delta P_{el}$ is used between the hot periods and cold periods. At the end of the initialization 610, a linear detection law (e.g., such as in the graph of FIG. 5a) may be obtained for the particular ambient temperature.

For example, during the initialization 610, the controller 250 may control a variable voltage subjected to the Joule-heated emitting electrical conductor 260 and modulated according to a duty cycle, the duty cycle being variable between:

a high-average power duty cycle during hot periods 472h, so that the Joule-heated emitting electrical conductor 260 is subjected to a high-average power to reach and maintain the emission temperature; and a low-average power duty cycle during cold periods 472c alternated to the hot periods 472h, so that the Joule-heated emitting electrical conductor 260 is subjected to a low-average power to reach a temperature smaller than the emission temperature, wherein the low-average power duty cycle is smaller than the high-average power duty cycle.

During the initialization procedure, the decrement between the high-average power and the low-average power may be maintained constant and the ambient temperature is also maintained constant. The controller 250 may be configured, during a measurement operation 620 (i.e., subsequently to the initialization 610), to define the low-average power duty cycle in such a way that the decrement between the high-average power and the low-average power is the same of the decrement between the high-average power and the low-average power experienced during the initialization procedure.

Analogously, the sensor 300 may be understood as being configured to perform the initialization procedure 610, wherein the initialization procedure 610 provides multiple emissions and detections, through the detector 300, for different known amounts of fluid, so as to individuate a detection law mapping amounts of fluid onto reading units to be converted into amounts of fluids. The sensor 300 may be configured, in operation, to define the low-average power duty cycle in such a way that the decrement between the high-average power and the low-average power is the same of the decrement between the high-average power and the low-average power experienced during the initialization procedure.

The initialization procedure 610 may operate like in the normal measurement operations 620. For example, the temperature measures 240' and/or the voltage measures 230' may be performed identically. In some examples, the initialization procedure 610 may be performed at a pre-defined ambient temperature and a pre-defined supply voltage $V_{DD}$, e.g. using high-precision machinery.

During measurement operations 620, the results obtained at the initialization 610 will be used. In particular, in operations, the emitter 100 will define the duty cycles so as to present the same constant decrement $\Delta P_{el}$, used in the initialization at any possible ambient temperature.

As can be seen in FIG. 6, the emission (step 634) operated as in FIG. 4 may be actually preceded by at least one of:
- a timeoff step 631, during which no voltage is provided to the heater 260 (e.g., the switch 212 is maintained open); the timeoff permits the heater 260 to reach the thermal equilibrium with the environment;
- at step 632, a temperature measurement (to achieve the value 230') and/or a voltage measurement (to achieve the value 240') being measured;
- at step 633, the high-average power duty cycles and low-average power duty cycle are defined based on the measurements 230' and 240'.

The iteration 635 refers to the fact that several pulses may be generated with the same pre-calculated duty cycles.

Even if not shown in FIG. 6, during the initialization 610 the detector 200 detects the signal 314 and provides the output based on the linear law previously defined.

In some examples, the initialization 610 is not necessary, and other methods may be used (e.g., reference data obtained by simulation, etc.). In some other examples, the initialization 610 may be performed multiple times (e.g., when it is intended to re-initialize the emitter).

FIGS. 5a, 5b, 5c, and 5d show four graphs which show advantages of embodiments of the invention.

The graph of FIG. 5a shows the linear function u [ordinate] which maps the real amount of gas [abscissa: ppm]. In principle (e.g., the technique discussed here), this graph is valid only at $T_{AMBIENT}=25°$ C. (which may be the ambient temperature at which the initialization 610 has been performed). As can be seen, u(ppm) follows linearly the real amount of gas, but is subjected to the offset at 0 ppm (i.e. u(0)>0). As explained above, the offset is proportional to the decrement $\Delta P_{el}$ of average electric power from a hot period to the subsequent cold period (i.e. $u(0) \propto \Delta P_{el}$). The slope of u(ppm) is proportional to the emission (hot) temperature (here indicated with $T_{max,25}$), i.e.

$$\frac{du}{dppm} \propto T_{max,25}$$

(where $T_{max,25}$ is the hot temperature reached by starting at 25° C., without the above discussed compensation at hot periods). The sensor 300 may have the knowledge of the graph of FIG. 5a.

Figure 5B:
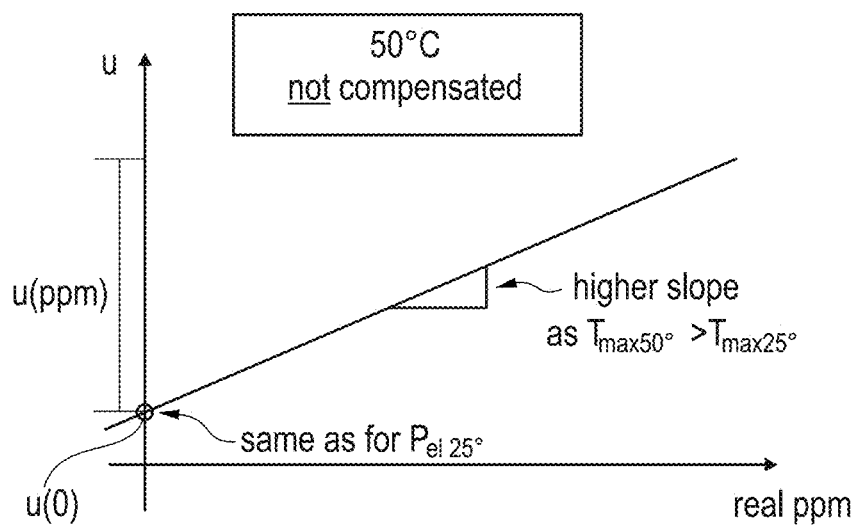

The graph of FIG. 5b shows the output when the ambient temperature is 50° C. (without the techniques discussed above, e.g. those that compensate the ambient temperature during the hot periods). If the different ambient temperature is not compensated and the duty cycle at the cold periods and the hot periods are not modified with respect to the case of the graph of FIG. 5a, by virtue of $T_{max,50}>T_{max,25}$ (where $T_{max,50}$ is the hot temperature reached by starting at 50° C., without the above discussed compensation at hot periods), the slope $$\frac{du}{dppm} \propto T_{max,50}$$

is increased: the new relationship is shown in the graph of FIG. 5b, but this time the sensor 300 has no knowledge of it, and it could provide an incorrect measurement 316.

Figure 5C:
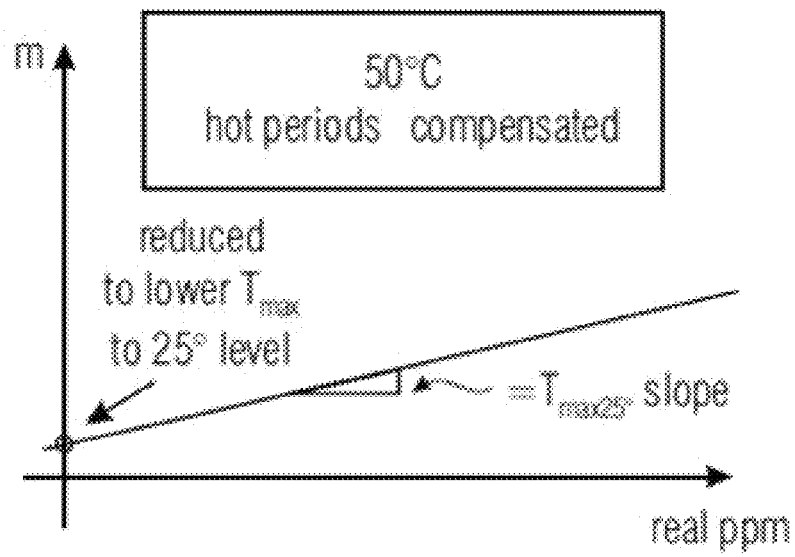

With the present techniques, however, it is possible to cope with this inconvenience at the emitter. The graph of FIG. 5c shows an advantageous effect of the present techniques (in particular the compensation at the hot periods). Here, with $T_{AMBIENT}=50°$ C. (like in the graph of FIG. 5b), at any ambient temperature the emitter is subjected to the same emission temperature $T_{HOT}=T_{max,25}$, and the slope can be reported to $$\frac{du}{dppm} \propto T_{max,25}.$$

This is the effect of having compensated the hot periods 472h by modifying the duty cycle to take into consideration the ambient temperature and the voltage at the heater 260. This result has been obtained by assuming that, in the cold periods, the conductor 260 is permanently off ($D_{COLD}=0$). However, unwantedly, the offset u(0) is not maintained constant but is reduced. This could also cause an incorrect reading of the amount of gas.

Figure 5D:
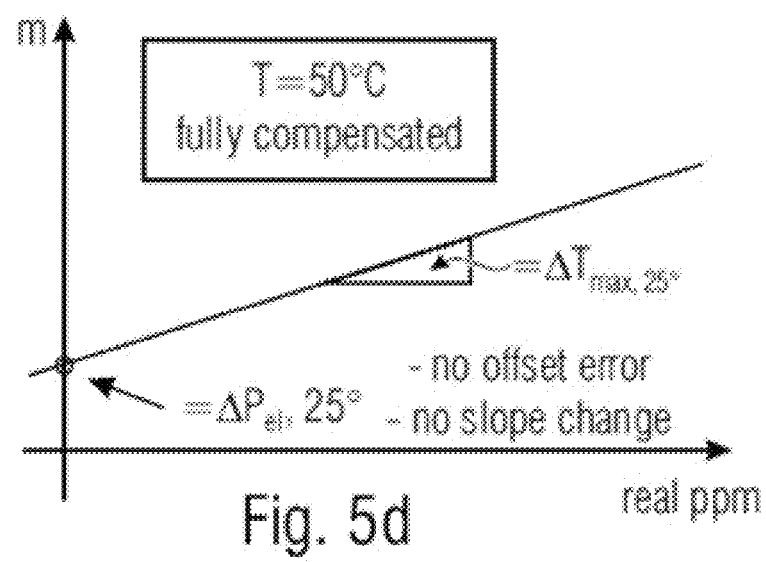

It has been understood that, by using, in the cold periods 472c, the low-average power duty cycle $D_{COLD}$ defined in such a way that the reduction of power is constant throughout the measurements (e.g. the same as in the initialization), also the offset diminution is compensated. The advantageous effect is depicted in the graph of FIG. 5d. As can be seen by comparing the graphs of FIG. 5a and FIG. 5d, at the ambient temperature of 50° C. the function u(ppm) appears the same of the function u(ppm) at the ambient temperature of 25° C. (i.e., no slope change and no offset error with respect to the situation in the graph of FIG. 5a).

Another example can be understood with the comparison of a $1^{st}$ scenario at $T_{AMBIENT,1st\ scenario}=25°$ C. and a $2^{nd}$ scenario at $T_{AMBIENT,2nd\ scenario}=50°$ C. At first, the hot periods are here taken into consideration:

$1^{st}$ scenario ($T_{AMBIENT, 1st\ scenario}$=25° C.), hot periods:
Peak (emission) temperature $T_{HOT}$=950° C.,
$\Delta T_{HOT}$=$T_{HOT}$−$T_{AMBIENT, 1st\ scenario}$=950° C.−25° C.=925° C.
Average power $P_{el,HOT,1st\ scenario}$ to reach $\Delta T_{HOT,1st\ scenario}$ is 400 mW (which is to be provided at the hot periods)

$2^{nd}$ scenario ($T_{AMBIENT}$=50° C.), hot periods:
Peak (emission) temperature $T_{HOT}$=950° C. (it shall stay constant, for permitting the emission at the necessary wavelength $\lambda_0$),
$\Delta T_{HOT}$=$T_{HOT}$−$T_{AMBIENT, 2nd\ scenario}$=950° C.−50° C.=900° C.
Average power $P_{el,HOT,2nd\ scenario}$ to reach $\Delta T_{HOT,1st\ scenario}$ is 390 mW Hence, the difference between the electrical power in the first scenario and the electrical power in the second scenario is determined to be $\Delta P_{el,HOT,1st\ scenario-2nd\ scenario}$=$P_{el,HOT,1st\ scenario}$−$P_{el,HOT,2nd\ scenario}$=400 mW−390 mW=10 mW. This $\Delta P_{el,HOT,1st\ scenario-2nd\ scenario}$ of 10 mW in the hot periods causes the offset drift at the detector, which sees the absolute power as a baseline u(0) (due to thermoacoustic phenomena).

The cold periods average power has to be adapted to cope with the thermoacoustic phenomena by choosing the following constant value 380 mW for $\Delta P_{el}$:

$1^{st}$ scenario ($T_{AMBIENT,1st\ scenario}$=25° C., for which the already calculated
$P_{el,hot,\ 1st\ scenario}$=400 mW, see above), cold periods:
"Pre-heating" to have a certain power level of e.g. 20 mW (e.g. giving $T_{COLD}$=85° C.)
$\Delta P_{el}$=$P_{el,HOT,1st\ scenario}$−$P_{el,COLD,1st\ scenario}$=400 mW−20 mW=380 mW ($\Delta P_{el}$ shall stay constant!)

$2^{nd}$ scenario ($T_{AMBIENT,2nd\ scenario}$=50° C., for which the already calculated
$P_{el,hot,1st\ scenario}$=390 mW, see above), cold periods:
"Pre-heating" at 10 mW (giving $T_{COLD}$=85° C. as the conductor 260 starts hotter by the ambient temperature but uses less power)
$\Delta P_{el}$=$P_{el,HOT,2nd\ scenario}$−$P_{el,COLD,2nd\ scenario}$=390 mW−10 mW=380 mW (same $\Delta P_{el}$ as at 25° C. ambient: target achieved)

Hence, $\Delta P_{el,HOT,1st\ scenario-2nd\ scenario}$≠0 would cause an unwanted offset drift, implying a deviation between of the input power, which is demanded to remain stable (in this case 380 mW). By keeping $\Delta P_{el}$=$P_{el,HOT}$−$P_{el,COLD}$=constant, it is possible to move from the situation of the graph of FIG. 5c to that of the graph of FIG. 5d: the offset and the slope end to be the same of the graph of FIG. 5a, and the amount of gas can be easily measured.

For example, the $1^{st}$ scenario is the scenario at the initialization 610, and the $2^{nd}$ scenario is the scenario during a measurement operation 620. The same, constant decrement of electrical power $\Delta P_{el}$ is kept as provided to the heater 260.

For a generic measurement, the following duty cycles may be defined:
during hot periods 472h, the duty cycle is defined so as to achieve the emission temperature $T_{HOT}$ by keeping into account the ambient temperature as measured and/or the input voltage, the electrical resistance, and the thermal resistance (e.g., based on a formula $$T_{HOT} = T_{AMBIENT} + R_{th,HOT} \cdot D_{HOT} \cdot \frac{V_{DD}^2}{R_{el,HOT}},$$

where $T_{HOT}$, $T_{AMBIENT}$, $R_{th,HOT}$, $V_{DD}$, $R_{el,HOT}$ are known and $D_{HOT}$ is the unknown); and/or
during the cold periods 472c, the duty cycle is defined so as to imply a decrement $\Delta P_{el}$ of electrical power which is constant (e.g., the one defined in the initialization 610), keeping into account the formula $$T_{COLD} = T_{AMBIENT} + R_{th,COLD} \cdot D_{COLD} \cdot \frac{V_{DD}^2}{R_{el,COLD}}.$$

For example, the compensation of $\Delta P_{el}$ (so that it remains constant) may be done when calculating the low-average power duty cycle $D_{COLD}$ (e.g. from $\Delta T_{COLD}$=$T_{COLD}$−

$$T_{AMBIENT} = R_{th,COLD} \cdot D_{COLD} \cdot \frac{V_{dd}^2}{R_{el,COLD}}).$$

The compensation of the $\Delta P_{el}$ may be performed on line, by increasing (or respectively reducing) the input power with the same absolute power in the cold periods and in the hot periods.

In one example, from the general formula $$P_{el} = D \cdot \frac{V_{DD}^2}{R_{el}}$$

the following equation can be obtained $$\Delta P_{el} = V_{dd}^2 \cdot \left( \frac{D_{HOT}}{R_{el,HOT}} - \frac{D_{COLD}}{R_{el,COLD}} \right)$$

and, by imposing $\Delta P_{el}$=constant and $D_{HOT}$ being previously calculated, $D_{COLD}$ can be obtained (e.g. at step 633).

Above, reference is often made to dynamically controlling duty cycles (e.g., in cold periods and hot periods). However, it is noted that there are several possible techniques for choosing the duty cycles. For example, it is not necessary that the duty cycle is varied abruptly (e.g., from the hot period to the cold period, or based on a detection of a voltage ripple, etc.). Also, the duty cycle may be smoothed, filtered, etc., and this also applies to the signals 230' and 240' which are taken into account for dynamically defining the duty cycle. Further different modulations may be chosen which are based on the same duty cycle, but this is known.

Important achievements are obtained at the emitter, since the generated radiations results substantially independent of the ambient temperature and the input voltage. Hence, embodiments of the invention can result valid also for an emitter which is used for emission generation, and which could also not be used for gas sensing (and independent from the results associated to the graphs of FIGS. 5a, 5b, 5c, and 5d, for example): what is obtained is notwithstanding an emitter which emits at a precise specific wavelength without negative effects due to the ambient temperature and the supply voltage. A stable emission source is generated which does not depend on ambient temperature and supply voltage.

In particular for a fluid (gas) sensor, the effects of the thermoacoustic waves are greatly reduced. The detector 300, placed in the same case of the emitter 200, would be otherwise subjected to the effects of the thermoacoustic waves. By defining a stable $\Delta P_{el}$, however, the effects of the thermoacoustic waves are compensated.

Moreover, DC/DC converters and Zener diodes may in principle be avoided, since variations of the supply voltage are compensated.

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a microprocessor, a programmable computer or an electronic circuit. In some examples, one or more of the most important method steps may be executed by such an apparatus.

Depending on certain implementation requirements, examples of the present techniques can be implemented in hardware or in software. The implementation can be performed using a digital storage medium, for example a floppy disk, a DVD, a Blu-Ray, a CD, a ROM, a PROM, an EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some examples according to the present techniques comprise a data carrier having electronically readable control signals, which are capable of cooperating with a programmable computer system, such that one of the methods described herein is performed.

Generally, examples of the present techniques can be implemented as a computer program product with a program code, the program code being operative for performing one of the methods when the computer program product runs on a computer. The program code may for example be stored on a machine-readable carrier.

Other examples comprise the computer program for performing one of the methods described herein, stored on a machine-readable carrier.

In other words, an example of the present techniques is, therefore, a computer program having a program code for performing one of the methods described herein, when the computer program runs on a computer.

A further example of the methods is, therefore, a data carrier (or a digital storage medium, or a computer-readable medium) comprising, recorded thereon, the computer program for performing one of the methods described herein. The data carrier, the digital storage medium or the recorded medium are typically tangible and/or non-transitionary.

A further example of the present techniques is, therefore, a data stream or a sequence of signals representing the computer program for performing one of the methods described herein. The data stream or the sequence of signals may for example be configured to be transferred via a data communication connection, for example via the Internet.

A further example comprises a processor, for example a computer, or a programmable logic device, configured to or adapted to perform one of the methods described herein.

A further example comprises a computer having installed thereon the computer program for performing one of the methods described herein.

A further example according to the present techniques comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some examples, a programmable logic device (for example a field programmable gate array) may be used to perform some or all of the functionalities of the methods described herein. In some examples, a field programmable gate array may cooperate with a microprocessor in order to perform one of the methods described herein. Generally, the methods are preferably performed by any hardware apparatus.

The apparatus described herein may be implemented using a hardware apparatus, or using a computer, or using a combination of a hardware apparatus and a computer.

The apparatus described herein, or any components of the apparatus described herein, may be implemented at least partially in hardware and/or in software.

The methods described herein may be performed using a hardware apparatus, or using a computer, or using a combination of a hardware apparatus and a computer.

The methods described herein, or any components of the apparatus described herein, may be performed at least partially by hardware and/or by software.

The above described examples are merely illustrative for the principles of the present techniques. It is understood that modifications and variations of the arrangements and the details described herein will be apparent to others skilled in the art. It is the intent, therefore, to be limited only by the scope of the impending patent claims and not by the specific details presented by way of description and explanation of the examples herein.

What is claimed is:

1. An emitter comprising:
   a Joule-heated emitting electrical conductor configured to emit radiation at a specific wavelength;
   a controller configured to control a variable voltage applied to the Joule-heated emitting electrical conductor and modulated according to a duty cycle, the duty cycle being variable between:
   a high-average power duty cycle, during hot periods, so that the Joule-heated emitting electrical conductor is subjected to a high-average power in order to reach and maintain an emission temperature so that the Joule-heated emitting electrical conductor emits the radiation at the specific wavelength; and
   a low-average power duty cycle, during cold periods alternated to the hot periods, so that the Joule-heated emitting electrical conductor is subjected to a low-average power in order to reach a temperature that is smaller than the emission temperature so that the Joule-heated emitting electrical conductor does not emit the radiation at the specific wavelength, wherein the low-average power duty cycle is smaller than the high-average power duty cycle; and
   a temperature sensor configured to obtain at least one temperature-indicative measured value indicative of an ambient temperature,
   wherein the high-average power duty cycle and the low-average power duty cycle are defined based on the at least one temperature-indicative measured value, and
   wherein the specific wavelength is a characteristic wavelength of a particular fluid.

2. The emitter of claim 1, wherein the controller is configured to define, for at least one hot period, the high-average power duty cycle as the duty cycle that is permitted to reach and maintain the emission temperature at the Joule-heated emitting electrical conductor.

3. The emitter of claim 1, wherein the controller is configured to define at least one of the high-average power duty cycle or the low-average power duty cycle based on the at least one temperature-indicative measured value so that a high ambient temperature is compensated through a low high-average power duty cycle, and a low ambient temperature is compensated through a high high-average power duty cycle.

4. The emitter of claim 1,
wherein the controller is configured to define at least one of the high-average power duty cycle or the low-average power duty cycle based on at least one voltage-indicative measured value indicative of the voltage so that a high voltage is compensated through a small duty cycle, and a small voltage is compensated through a high duty cycle, and
wherein the controller is configured to obtain the at least one voltage-indicative measured value before a start of an application of the voltage to the Joule-heated emitting electrical conductor.

5. The emitter of claim 1,
wherein the controller is configured to define, for the cold periods, the low-average power duty cycle as a duty cycle causing a decrement of electrical power with respect to the high-average power, and
wherein the decrement is constant irrespective of the ambient temperature.

6. The emitter of claim 1, wherein the temperature sensor is configured to obtain the at least one temperature-indicative measured value as a value indicative of a temperature of the joule-heated emitting electrical conductor before starting to apply the variable voltage to the joule-heated emitting electrical conductor.

7. The emitter of claim 6, wherein the temperature sensor is configured to obtain the temperature-indicative measured value after a time period, which is sufficient to permit the joule-heated emitting electrical conductor to be in thermal equilibrium with an ambient.

8. The emitter of claim 6, wherein the controller is configured to define the high-average power duty cycle and the low-average power duty cycle before starting to apply the variable voltage to the joule-heated emitting electrical conductor.

9. The emitter of claim 1,
wherein the controller is configured to define the low-average power duty cycle and the high-average power duty cycle so as to cause a power loss of the Joule-heated emitting electrical conductor for a pre-fixed decrement of electrical power from the high-average power to the low-average power, and
wherein the pre-fixed decrement is constant irrespective of the ambient temperature.

10. A sensor configured to determine the characteristic wavelength of the fluid, the sensor comprising:
the emitter of claim 1;
a detector configured to detect an electric signal associated with the radiation at the specific wavelength; and
a target volume containing a target fluid, the target volume disposed between the emitter and the detector so that the radiation at the specific wavelength propagates through the target volume,
wherein the specific wavelength is a characteristic wavelength of the target fluid, and
wherein the electric signal is associated with characteristics of the fluid.

11. A method for the sensor of claim 10, the method comprising:
generating, during an initialization phase, multiple emissions and detections for different known amounts of fluids so as to individuate a detection law mapping amounts of fluids onto reading units to be converted into amounts of fluids,
wherein the method, during an operation phase, comprises defining the low-average power duty cycle such that a decrement between the high-average power and the low-average power is the same as the decrement between the high-average power and the low-average power experienced during the initialization phase.

12. A method comprising:
controlling, during an initialization phase, a variable voltage applied to a Joule-heated emitting electrical conductor and modulated according to a duty cycle, the duty cycle being variable between:
a high-average power duty cycle during hot periods so that the Joule-heated emitting electrical conductor is subjected to a high-average power in order to reach and maintain an emission temperature so that the Joule-heated emitting electrical conductor emits a radiation at a specific wavelength; and
a low-average power duty cycle during cold periods alternated to the hot periods, so that the Joule-heated emitting electrical conductor is subjected to a low-average power in order to reach a temperature smaller than the emission temperature so that the Joule-heated emitting electrical conductor does not emit the radiation at the specific wavelength,
wherein the low-average power duty cycle is smaller than the high-average power duty cycle, and
wherein, during the initialization phase, a decrement between the high-average power and the low-average power is maintained constant and an ambient temperature is also maintained constant; and
defining, during an operation phase, the low-average power duty cycle such that a decrement between the high-average power and the low-average power is the same as the decrement between the high-average power and the low-average power during the initialization phase,
wherein the specific wavelength is a characteristic wavelength of a particular fluid.

13. A method comprising:
emitting, by a Joule-heated emitting electrical conductor, a radiation at a specific wavelength at an emission temperature, wherein emitting is subjected to a duty cycle, the duty cycle being variable between:
a high-average power duty cycle during hot periods so that the Joule-heated emitting electrical conductor is subjected to a high-average power in order to reach the emission temperature so that the Joule-heated emitting electrical conductor emits the radiation at the specific wavelength; and
a low-average power duty cycle during cold periods alternated to the hot periods so that the Joule-heated emitting electrical conductor is subjected to a low-average power to reach a temperature smaller than the emission temperature so that the Joule-heated emitting electrical conductor does not emit the radiation at the specific wavelength,
wherein the high-average power duty cycle and the low-average power duty cycle are defined based on at least one temperature-indicative measured value indicative of a measured ambient temperature, and wherein the radiation at the specific wavelength is a characteristic wavelength of a fluid.

14. A sensing method for determining a characteristic of the fluid, the method comprising:
performing the method of claim 13,
propagating the radiation through a target volume containing a target fluid; and
detecting an electric signal associated with the radiation at the specific wavelength so that the electric signal is associated with the characteristic of the fluid.

15. A non-transitory storage unit storing instructions which, when running on a computer, cause the computer to perform the method of claim 13.

\* \* \* \* \*